United States Patent
Schaffar

(10) Patent No.: US 6,861,232 B2
(45) Date of Patent: Mar. 1, 2005

(54) CREATININE BIOSENSOR

(75) Inventor: Berhard Peter Harald Schaffar, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 26 days.

(21) Appl. No.: 10/031,516

(22) PCT Filed: May 14, 2001

(86) PCT No.: PCT/AT01/00138

§ 371 (c)(1),
(2), (4) Date: Jul. 21, 2002

(87) PCT Pub. No.: WO01/87300

PCT Pub. Date: Nov. 22, 2001

(65) Prior Publication Data

US 2003/0027239 A1 Feb. 6, 2003

(30) Foreign Application Priority Data

May 16, 2000 (AT) ......................................... A 853/2000

(51) Int. Cl.[7] .......................... G01N 33/53; C12Q 1/37; C12N 11/18; C12N 11/14; C12N 1/00
(52) U.S. Cl. ...................... 435/7.91; 435/24; 435/175; 435/176; 435/817
(58) Field of Search ........................ 435/7.91, 24, 175, 435/176, 212, 817

(56) References Cited

U.S. PATENT DOCUMENTS 5,466,575 A   11/1995  Cozzette et al. ............... 435/6
6,241,863 B1 * 6/2001  Monbouquette ......... 205/777.5

FOREIGN PATENT DOCUMENTS

FR          2682765 A1    4/1993    ......... G01N/27/327

OTHER PUBLICATIONS

Sirkir et al. "Glucose and Lactate Biosensors Based on Redox Polymer/Oxidoreductase Nanocomposite Thin Films," Anal. Chem. (2000) 72(13): 2930–2936.*
Armstrong et al. "Recent Developments in Faradaic Bio-electrochemistry," Electrochimica Acta (2000) 45:2623–2645.*
Okahata et al. "Preparations of Langmuir–Blodgett Films Enzyme–Lipid Complexes: A Glucose Sensor Membrane," Thin Solid Films (1989) 180: 65–72.*
Surareugchai et al. "Dual Electrode signal–subtracted biosensor for simultaneous flow injection determination of surcrose and glucose," Anal. Chimica Acta (1999) 380(1): 7–15.*
Tsuchida, Toshio et al., "Multi–Enzyme Membrane Electrodes for Determination of Creatinine and Creatine in Serum" Clinical Chemistry, vol. 29, No. 1 1983 (pp. 51–55).

* cited by examiner

Primary Examiner—Jean C. Witz
Assistant Examiner—Susan Hanley
(74) Attorney, Agent, or Firm—Sujatha Suhrameniam; Roche Diagnostics Operations, Inc.

(57) ABSTRACT

The present invention generally relates to a method for producing biosensors and a biosensor for determination of creatinine. The biosensor comprises at least two enzymes, for the amperometric determination of enzymatically degradable substances in biological liquids, the enzymes being immobilized on a working electrode.

13 Claims, No Drawings

CREATININE BIOSENSOR

BACKGROUND OF THE INVENTION

This invention relates to a method for producing biosensors comprising at least two enzymes, for the amperometric determination of enzymatically degradable substances in biological liquids, the enzymes being immobilized on a working electrode. Furthermore, the invention relates to a biosensor, in particular for the determination of creatinine.

BACKGROUND

The determination of enzymatically degradable substances, such as creatinine, glucose etc., by means of sensors in biological liquids, for example in blood, urine, plasma, serum and liquor, is preferably carried out via biosensors comprising immobilized enzymes. From the literature, several electrochemical and photometric methods of determining those substances are known.

Similarly, creatinine may be potentiometrically determined, for example by means of the enzyme creatinine deiminase, involving a subsequent determination of the ammonium content. Another method consists in determining the creatinine concentration by means of an enzyme cascade using the enzymes creatininase, creatinase and sarcosine oxidase, with hydrogen peroxide ($H_2O_2$) being finally measured at an amperometric electrode.

This invention relates to a method for producing biosensors that function in accordance with the last-mentioned principle. In doing so, the enzymes must be coimmobilized in order to allow for the conversion of creatinine to the amperometrically detectable molecule hydrogen peroxide. The conversion of creatinine to hydrogen peroxide is carried out according to the following reaction steps:

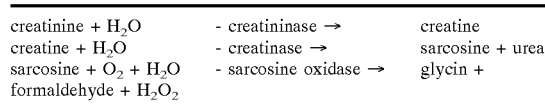

At the amperometric electrode, hydrogen peroxide is oxidized anodically against Ag/AgCl at −350 mV. The current flowing thereby is proportional to the creatinine concentration.

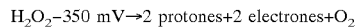

The oxygen recovered during the electrode reaction is then used for the oxidation of the sarcosine.

In the state of the art, various ways of immobilizing the three enzymes used are known. According to T. Tsuchida, K. Yoda, Clin. Chem. 29/1, p.51, 1983, all three enzymes are cross-linked with glutardialdehyde.

However, that sensor produced in such a manner discussed in the above cited reference has numerous drawbacks, only a low signal height is reached, i.e. only a slight change in current is ascertainable since the sarcosine oxidase immobilized in that manner loses almost its entire activity. However, a greatest possible signal height is particularly important especially for the determination of creatinine, since the concentration of creatinine is very small, especially in blood (approximately 50 $\mu M$), and, in addition, creatinase is available only with very small specific activities (20 iu/mg at the most). Furthermore, a sensor immobilized in such a manner exhibits long response times.

In U.S. Pat. No. 5,466,575, a method is described in which sarcosine oxidase and creatininase are immobilized in a fish gelatin capable of being subjected to light-induced crosslinking and subsequently are superimposed by creatinase in a film-forming polyvinyl-acetate-co-vinyl-alcohol latex. However, one major drawback with this method is the production of the biosensor is very complicated due to light-induced crosslinking.

SUMMARY OF THE INVENTION

The object of the invention is to provide a method of the initially mentioned kind which overcomes the above-mentioned drawbacks and difficulties. In particular, the method according to the invention is to allow for a simple production of a biosensor with which both short response times and great signal heights are achievable. In particular, immobilizing the enzymes at room temperature is to be possible.

According to the invention, that object is achieved in that an enzyme together with one or more surface-active substances in an aqueous solution is applied on the working electrode and is allowed to dry, and the at least second enzyme is chemically immobilized thereupon in a subsequent step.

DETAILED DESCRIPTION OF THE INVENTION

For the purposes of the present description and patent claims, the term "surface-active substances" is to cover substances which possess surface-active characteristics, such as detergents and alcohols, for example glycerine.

Preferably, polyalcohols and/or detergents, preferably non-ionic tensides, are used as surface-active substances.

It has been found out that, by means of those additives, the measured current is increased by a factor of about 40 in comparison to biosensors comprising three equally immobilized enzymes.

Suitably, the at least second enzyme is immobilized by means of crosslinking, covalent binding or matrix inclusion. Preferably, immobilization is brought about by glutardialdehyde.

In a preferred embodiment, a cover membrane is applied after immobilization of the enzymes. Such a membrane consisting, for example, of nafion, PVC copolymer or cellulose acetate advantageously increases the linearity of the sensors and, in addition, causes a reduction of interfering influences.

A biosensor according to the invention which comprises a working, a reference and a counter electrode and whose enzymes have been immobilized by means of the method according to the invention is characterized in that the reference electrode is an Ag/AgCl electrode, the counter electrode is a carbon electrode, the working electrode consists of carbon, metal, metal oxides or a mixture of carbon and metal or metal oxides and the electrodes are applied on a nonconducting substrate.

In particular, a biosensor according to the invention for the determination of creatinine is characterized in that sarcosine oxidase is adsorbed on the working electrode and creatininase and creatinase are immobilized thereupon.

In a preferred embodiment, the biosensor is made up of two thee-electrodes systems, the first electrode system comprising the enzymes creatininase, creatinase and sarcosine oxidase and serving for the determination of the sum of creatinine and creatine and the second electrode system comprising the enzymes creatinase and sarcosine oxidase and serving for the determination of creatine, whereby the result of the second electrode system is deducted from the result of the first one for the determination of creatinine.

Advantageously, the biosensor comprises a further electrode system serving for the elimination of electrochemical interferences.

In the following, the invention is explained further by the aid of the following examples:

EXAMPLE 1

Example 1 shows the improvement of the signal height by increasing the activity of the sarcosine oxidase when adding, in accordance with the invention, surface-active substances, as opposed to the prior art.

Sarcosine oxidase dissolved in water (prior art) as well as in water with water-soluble, surface-active components (in the instant case, glycerine as well as three non-ionic tensides) being added was dropped onto the amperometric base sensor and was allowed to dry at room temperature. Upon polarization of the electrode, the current was measured on 1 mM sarcosine. The measuring result is shown in Table 1.

TABLE 1

| Sarcosine oxidase (SOx) | Additive | Current on 1 mM sarcosine |
| --- | --- | --- |
| 54.2 mg SOx in 0.5 ml $H_2O$ | none | 2 nA |
| 54.2 mg SOx in 0.5 ml $H_2O$ | 5.0% glycerine | 80 nA |
| 54.2 mg SOx in 0.5 ml $H_2O$ | 0.5% Tween 20 | 70 nA |
| 54.2 mg SOx in 0.5 ml $H_2O$ | 0.5% Triton X100 | 90 nA |
| 54.2 mg SOx in 0.5 ml $H_2O$ | 0.5% Brij 35 | 85 nA |

It was found that the current on 1 mM sarcosine could be increased by a factor of about 40 by means of detergents or glycerine, respectively.

Apparently, that enormous increase in current has been achieved since, during drying, the enzyme is protected in the best possible way by the additives and since the surface-active characteristics of the additives result in a better and closer bonding with the porous texture of the hydrogen peroxide electrode.

EXAMPLE 2

Example 2 shows the improvement of the signal height as well as the shortening of the response time of a biosensor according to the invention in comparison to a biosensor produced in accordance with the prior art (T. Tsuchida).

Two complete creatinine sensors were produced, whereby, in case of the first sensor, all three enzymes together were cross-linked with glutardialdehyde and, in case of the second sensor, sarcosine oxidase with Tween 20 was first applied on the base electrode and subsequently creatininase and creatinase were immobilized thereupon with glutardialdehyde. The resulting currents and response times, respectively, for measuring creatinine as well as sarcosine are listed in Table 2.

TABLE 2

| Sarcosine oxidase | Current on 1 mM creatinine | Current on 1 mM sarcosine | Response time (T90) |
| --- | --- | --- | --- |
| in glutardialdehyde (sensor 1) | 120 nA | 140 nA | 80 s |
| in Tween 20 (sensor 2) | 420 nA | >500 nA | 10 s |

By means of the immobilization according to the invention of the enzymes, a by far stronger current was measured. The response time of the sensor produced according to the invention was also clearly shorter than that of the sensor known in the prior art.

EXAMPLE 3

In example 3, the production of a creatinine biosensor according to the invention is described.

By means of the serigraphy process, Ag-strip conductors for reference, counter and working electrodes were printed on an electrically nonconducting substrate made of a synthetic or ceramic material. The reference electrode is produced from an Ag/AgCl-paste at least in the sensor area A layer of carbon paste is printed on the counter electrode within its measuring area. By means of the same carbon paste, the Ag-strip conductor of the working electrode is extended into the measuring area In the measuring area of the working electrode, a mixture of 5% manganese dioxide in carbon paste is printed as a working electrode. Subsequently, the entire system with the exception of the electrode spots lateron to be contacted with a liquid and the strip conductors serving for the signal tap is repeatedly coated with an insulating varnish. Following that, sarcosine oxidase in a Tween 20 solution is dropped onto the working electrode and is allowed to dry. Thereupon, the other enzymes are immobilized by means of glutardialdehyde. In order to increase linearity and to reduce interfering influences, a cover membrane is applied.

In order to be able to determine creatinine without any interferences, at least two three-electrodes systems are necessary; one system comprising the enzymes creatininase, creatinase and sarcosine oxidase which determines creatinine and creatine as well another one comprising the enzymes creatinase and sarcosine oxidase which serves for the determination of creatine. Since creatine acts as an interfering substance in blood, the measured creatine value has to be deducted from the measured value of the creatinine electrode, which is composed of creatine and creatinine.

In order to eliminate further electrochemical interferences, a third electrode system may be used solely with immobilized sarcosine oxidase (creatine is replaced by an inactive protein, for example albumin).

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for producing biosensors comprising at least two enzymes for the amperometric determination of enzymatically degradable substances in biological liquids wherein the enzymes are immobilized on a working electrode, comprising applying an enzyme together with one or more surface-active substances in an aqueous solution on the working electrode, allowing said enzyme together with the one or more surface-active substances in the aqueous solution to dry, and chemically immobilizing the at least second enzyme thereupon.

2. The method according to claim 1, wherein polyalcohols, detergents, or a combination thereof are used as surface-active substances.

3. The method according to claim 2, wherein non-ionic tensides are used as surface-active substances.

4. The method according to claim 2, further comprising applying a cover membrane after immobilization.

5. The method according to claim 1, wherein the at least second enzyme is immobilized by crosslinking, covalent binding or matrix inclusion.

6. The method according to claim 5, wherein the at least second enzyme is immobilized by glutardialdehyde.

7. The method according to claim 5, further comprising applying a cover membrane after immobilization.

8. The method according to claim 2, wherein the at least second enzyme is immobilized by crosslinking, covalent binding or matrix inclusion.

9. The method according to claim 8, further comprising applying a cover membrane after immobilization.

10. A biosensor comprising a working, a reference and a counter electrode, produced by means of the method according claim 1, wherein the reference electrode is an Ag/AgCl electrode and the counter electrode is a carbon electrode and the working electrode consists of carbon, metal, metal oxides or a mixture of carbon and metal or metal oxides, the electrodes being applied on a nonconducting substrate.

11. A biosensor according to claim 10 for the determination of creatinine, wherein sarcosine oxidase is adsorbed on the working electrode and creatininase and creatinase are immobilized thereupon.

12. A biosensor according to claim 11, wherein it is made up of two three-electrodes systems, the first electrode system comprising the enzymes creatininase, creatinase and sarcosine oxidase and serving for the determination of the sum of creatinine and creatine and the second electrode system comprising the enzymes crease and sarcosine oxidase and serving for the determination of creatine, whereby the two results are subtracted for the determination of creatinine.

13. A biosensor according to claim 12 which comprises a further electrode system serving for the elimination of electrochemical interferences.

* * * * *